(12) United States Patent
Young

(10) Patent No.: US 6,466,923 B1
(45) Date of Patent: Oct. 15, 2002

(54) METHOD AND APPARATUS FOR BIOMATHEMATICAL PATTERN RECOGNITION

(75) Inventor: Fredric S. Young, Los Altos, CA (US)

(73) Assignee: Chroma Graphics, Inc., Burlingame, CA (US)

( * ) Notice: Subject to any disclaimer, the term of this patent is extended or adjusted under 35 U.S.C. 154(b) by 0 days.

(21) Appl. No.: 09/070,110

(22) Filed: Apr. 29, 1998

Related U.S. Application Data

(60) Provisional application No. 60/090,528, filed on May 12, 1997.

(51) Int. Cl.[7] ............................................. G06N 3/00
(52) U.S. Cl. ......................... 706/13; 706/20; 382/103; 382/194
(58) Field of Search .................... 706/13, 20; 382/103, 382/194

(56) References Cited

U.S. PATENT DOCUMENTS

| | | | |
|---|---|---|---|
| 4,697,242 A | 9/1987 | Holland et al. | 364/513 |
| 4,821,333 A | 4/1989 | Gillies | 382/49 |
| 5,222,192 A | 6/1993 | Shaefer | 395/13 |
| 5,375,195 A | 12/1994 | Johnston | 395/135 |
| 5,400,436 A | 3/1995 | Nara et al. | 395/13 |
| 5,448,668 A | 9/1995 | Perelson et al. | 395/182.19 |
| 5,479,523 A | 12/1995 | Gaborski et al. | 382/159 |
| 5,581,657 A | 12/1996 | Lyon | 395/13 |
| 5,623,513 A | 4/1997 | Chow et al. | 375/219 |
| 5,700,637 A | 12/1997 | Southern | 435/6 |
| 5,768,318 A | 6/1998 | Mestdagh | 375/296 |
| 5,787,113 A | 7/1998 | Chow et al. | 375/219 |
| 5,830,645 A | 11/1998 | Pinkel et al. | 435/6 |
| 5,835,536 A | 11/1998 | May et al. | 375/316 |
| 5,845,049 A | * 12/1998 | Wu | 706/20 |
| 5,853,979 A | 12/1998 | Green et al. | 435/5 |
| 5,864,630 A | * 1/1999 | Cosatto et al. | 382/103 |
| 5,864,633 A | 1/1999 | Opsal et al. | 382/141 |
| 6,021,220 A | * 2/2000 | Anderholm | 382/194 |

OTHER PUBLICATIONS

Lank, E.; Blostein, D., N–grams: a well–structured knowledge representation for recognition of graphical documents, Document Analysis and Recognition, 1997., Proceedings of the Fourth International Conference on, vol.: 2., 1997, pp.: 801–804 vol. 2, Jan. 1997.*

* cited by examiner

Primary Examiner—Mark Powell
Assistant Examiner—Wilbert Starks
(74) Attorney, Agent, or Firm—Townsend and Townsend and Crew LLP; Kenneth R. Allen

(57) ABSTRACT

In an analysis of a set of discrete multidimensional data which can be represented in an array with a topology, where the array that can be mapped to an image space of discrete elements, such as digitized image data, seismic data and audio data, genotype/phenotype classifications are imposed on the topology, and then molecular biological-like processes (annealing, fragmentation, chromatographic separation, fingerprinting, footprinting and filtering) are imposed upon that topology to perceive classifiable regions such as edges. More specifically, an image feature probe constructed of strings of contiguous image fragments of the class of N-grams called linear N-grams, anneals genotypes of topological features by complementary biological-like techniques in the same manner that complex biological systems are analyzed by genetic mapping, sequencing and cloning techniques. For example, molecular biological probes anneal with molecular biological genotypes and then are used to classify those genotypes. More specifically, an image feature probe constructed of strings of contiguous pixels, of the class of N-grams called linear N-grams, mates genotypes of topological features by complementary biological-like techniques in the same manner that molecular biological probes mate with molecular biological genotypes. The topological genotypes are by definition orthogonal elements to edges. Techniques are disclosed for defining the feature probes.

16 Claims, 11 Drawing Sheets

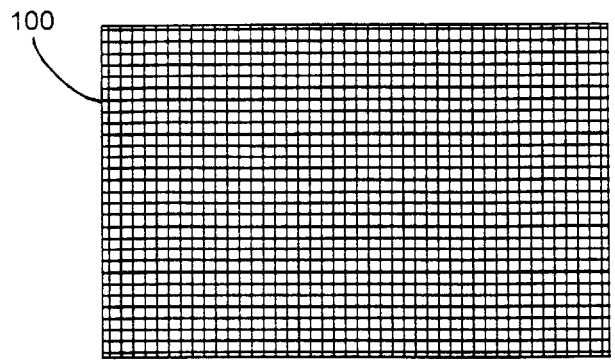
FIG. 6A
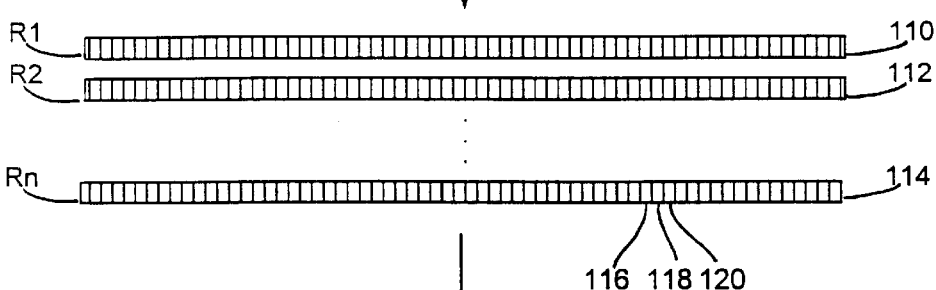
FIG. 6B
FIG. 6C
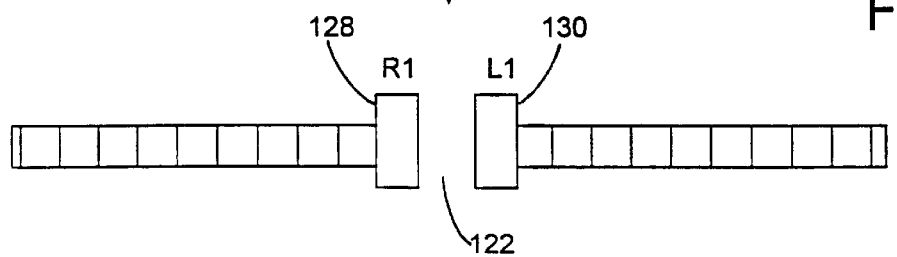
FIG. 6D
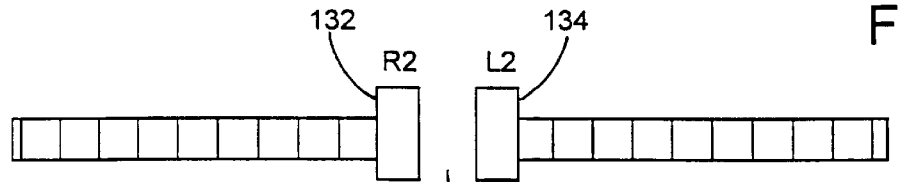
FIG. 6E
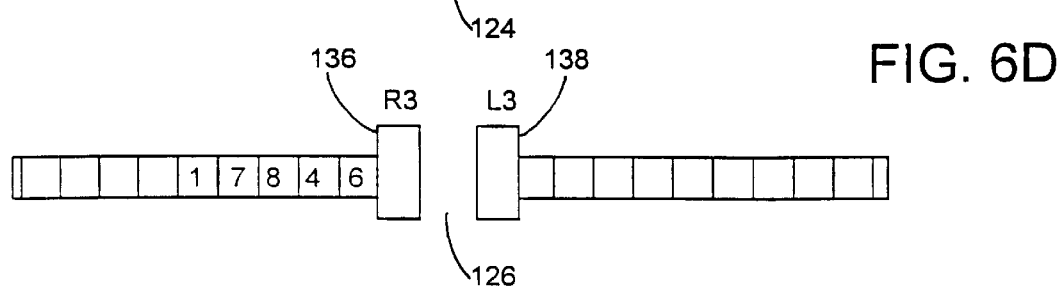

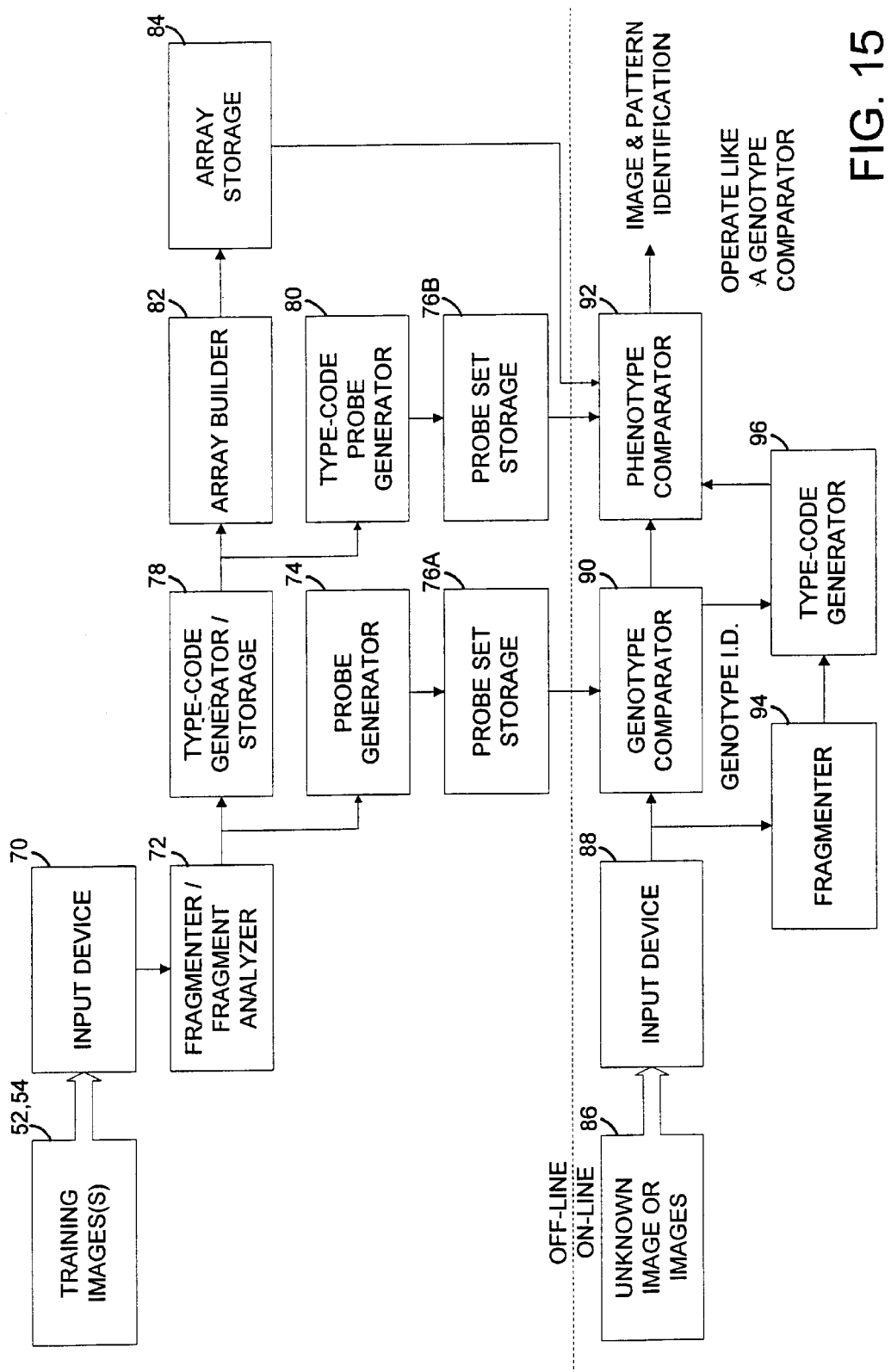

METHOD AND APPARATUS FOR BIOMATHEMATICAL PATTERN RECOGNITION

This disclosure claims the benefit of Patent Application Ser. No. 60/090,528 filed May 12, 1997 as a provisional patent application.

BACKGROUND OF THE INVENTION

This invention relates to pattern recognition and more particularly this invention relates to applications of mathematical techniques based on molecular genetics.

It has been observed that certain genetic processes can be described and analyzed mathematically, particularly by nonlinear mathematics. It has been observed that there are underlying similarities between digital information and molecular genetics. An example is the discovery that actual molecular biological reactions can be used to solve mathematical problems, such as the "traveling salesman" routing problem. (Dr. Leonard Adleman, a computer scientist at U.S.C., created an artificial DNA string for each node in a space and allowed the DNA strings to combine to define a singular path. L. Adleman, "Molecular Computation of Solutions to Combinatorial Problems." *Science* Magazine. Vol. 266, Nov. 11, 1994.)

U.S. Patents and references were identified in an investigation of the prior art and are cited to the U.S. Patent Office in a separate Invention Disclosure Statement. Nothing showed the use of biomathematical techniques for texture or pattern recognition.

Of the references uncovered, U.S. Pat. No. 5,375,195 to Johnston shows the use of "genetic algorithms" to effect facial recognition, drawing on the techniques of mutation, phenotyping, gene, genotyping and crossover with mathematical processes. The use of the term "genetic algorithm" therein and elsewhere in the literature refers to recombining and selecting functions which mimic the processes occurring in natural genetic reproduction in living organisms.

The only known precedent for the use of the term "genetic algorithm" beyond the conventional use as in Johnston is in Adleman's work in solution of the Hamiltonian path problem. The equivalent term for Adleman's process is "molecular computation." Adleman's work has spawned a new field of research investigation, which so far has lead to computational tools and elements, which is reported in the research science literature. An example is the proceedings of the Discrete Mathematics and Computer Science Workshop held Apr. 4, 1995 at Princeton University.

A 1981 Ph.D. dissertation entitled "Computational Models for Texture Analysis and Texture Synthesis" by David Garber at the University of Southern California discussed the concept of the use of N-gram statistics in texture analysis and generation. His analysis used a technique involving a maximum of N equal to four pixels in a row to determine fourth order statistical analysis to extract parameter sets in texture generation. He was able to correlate textures of different orders based on statistical analysis of pixel groupings. While never treated as image fragments, the present inventor has recognized a relationship between the concept of N-grams and the pixel groupings of contiguous pixels used in the present invention to create probes.

What is needed is an improved method to solve mathematically-challenging pattern problems, such as pattern recognition problems, including "edge" detection within a dataset (rather "edge" detection on a physical structure) wherein the dataset has an unarticulated but definable topology. The following invention exploits similarities between the genetic pattern recognition problems in the realm of image topology, where the topology is a function of relationships between pixels of an image.

SUMMARY OF THE INVENTION

According to the invention, in an analysis of a set of discrete multidimensional data which can be represented in an array with a topology, where the array that can be mapped to an image space of discrete elements, such as digitized image data, seismic data and audio data, genotype/phenotype classifications are imposed on the topology, and then molecular biological-like processes (annealing, fragmentation, chromatographic separation, fingerprinting, footprinting and filtering) are imposed upon that topology to perceive classifiable regions such as edges. More specifically, an image feature probe constructed of strings of contiguous image fragments of the class of N-grams called linear N-grams, anneals genotypes of topological features by complementary biological-like techniques in the same manner that complex biological systems are analyzed by genetic mapping, sequencing and cloning techniques. For example, molecular biological probes anneal with molecular biological genotypes and then are used to classify those genotypes. These topological genotypes are by definition orthogonal elements to edges.

The image fragments may be resolution independent. However, the image fragments can likewise be pixel strings where the pixels delimit the resolution of the image. Nevertheless, the probe derived from the image fragment can be constructed with an informational vector that is not limited by the resolution of the pixel representation. It is merely necessary that any informational vector, such as shape defined as a gradient in an analysis space, be compatible with the analysis space.

In the present invention, the process of applying genetic analysis techniques is analogized in the realm of digital computing, including the mimicking of functions carried out by molecular biologists in genetic analysis for biotechnology. Some of these techniques may be based on natural processes carried out by extra-chromosomal genetic elements. Some techniques have also been engineered by researchers. The genetic analysis techniques of the present invention are used for the image processing needed in pattern recognition and in particular texture recognition. Various methods for constructing probes are described.

The provisional application described a process involving a probe constructed from image fragment data to yield a type code. The present description further expounds on that description by recognizing that two types of information can be derived from a data array (such as pixel image data) to form a probe to yield a type code. The sequence that makes up a probe can be a sequence of entities (pixels) in an array and a sequence of differences between entities of the array.

The invention will be better understood upon reference to the following description in connection with the accompanying drawings.

BRIEF DESCRIPTION OF THE DRAWINGS

FIGS. 6A–6E are an illustration on an image of the steps of fragmentation and end labeling.

FIG. 15 is a block diagram of an apparatus for performing the processes according to the invention.

DESCRIPTION OF SPECIFIC EMBODIMENTS

In order to understand the invention, it is useful to define the underlying components. In this invention, which relates to image analysis, and in particular to two-dimensional image analysis, the characteristics of genotypes and phenotypes which are found in biological systems are exploited in "genotype"-like and "phenotype"-like formations in digitized information. An image or data genotype of a feature in an image is a set of elemental sequences which uniquely define the feature. An image or data phenotype is the observable expression of a feature. Two distinguishable phenotypes will have distinguishable genotypes. By building probes to search for such unique genotypes, unique and distinguishable phenotypes can be identified.

Figure 1:
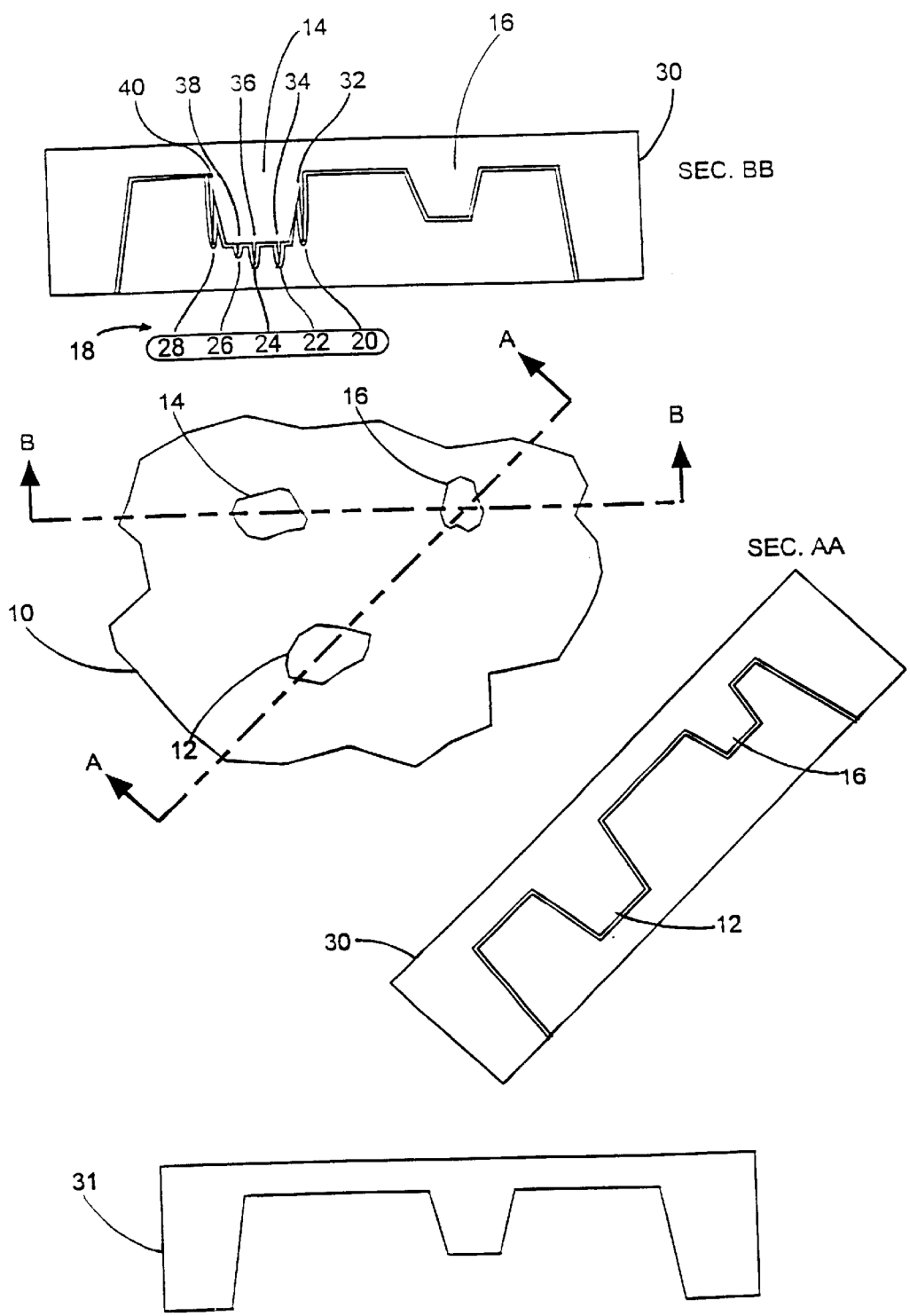
FIG. 1 is a diagram of a topology illustrating genotypes and probes.

Referring to FIG. 1, there is shown a top view of an image 10 with sections A—A and B—B demarcated through different pattern features 12, 14, 16. The image pattern features 12, 14, 16 may be color (chrominance) or density (luminance) characteristics. Sections are drawn through different features. The image with its features is recognizable at a macroscopic level. At the image feature level (wherein sequences of pixels are grouped into recognizable elements), the image and its features are analogous to a phenotype. At the fully magnified level, values of individual pixels can be deciphered. When in this form, the information is analogous to a genotype. A genotype 18 is a definable sequence, as hereinafter explained, of pixels 20, 22, 24, 26, 28 in or around features, such as feature 14. (The illustration is not to scale, since a phenotype is typically not recognizable when viewed at the resolution needed to resolve a genotype, and a genotype cannot be observed when viewed at a resolution suited to resolve a phenotype.)

The Pattern/Texture Recognition Process

According to one aspect of the invention, a probe 30 is provided which is complementary at the genotype level with aspects of the image 10 to be recognized, which probe is then used to recognize a pattern or more specifically a texture. The probe is a very powerful tool. Therefore, most of the interest in this invention will be in the techniques for developing probes, particularly probes which are based, either directly or indirectly, on source patterns to be recognized.

At the genotype level, the probe 30 is observed to have a complementary value at each pixel position 32, 34, 36, 38, 40 to a substantial fraction of the image pixels 20, 22, 24, 26, 28 in "key" features (e.g., features 12, 14 and 16) in the image 10. It is not contemplated that a match will be found at all positions in an image, so long as at least certain key features "match" with the probe, in accordance with the matching criteria which may be established according to the invention. It should be understood that there may be more than one probe, e.g., probes 30, 31, which are available in order to identify more than one image or pattern within an image. Real features, as herein referred to as phenotypes, may well require a plurality of probes to completely analyze. Similarly, a single probe could function as a "filter" to search for a single feature unique to a sought-for image among a set of images.

In order for the probes to function across the optimum set of images or data sets, the probes are normalized upon creation in terms of orientation and size (image resolution) in physical or mathematical space, respectively. Images, having been digitized into data are treated as data sets. The data sets of N dimensions are decomposed into normalized matrixes of N–1 dimensions vectors for processing in a manner to match the normalization of the probe set. (For example a two-dimensional image is decomposed into a one-dimensional vector along the normalized axis corresponding to the probe set wherein the probe set and the image are aligned to a common, generally fixed reference, such as compass direction or gravity.)

Developing a Basic Probe

Figure 2:
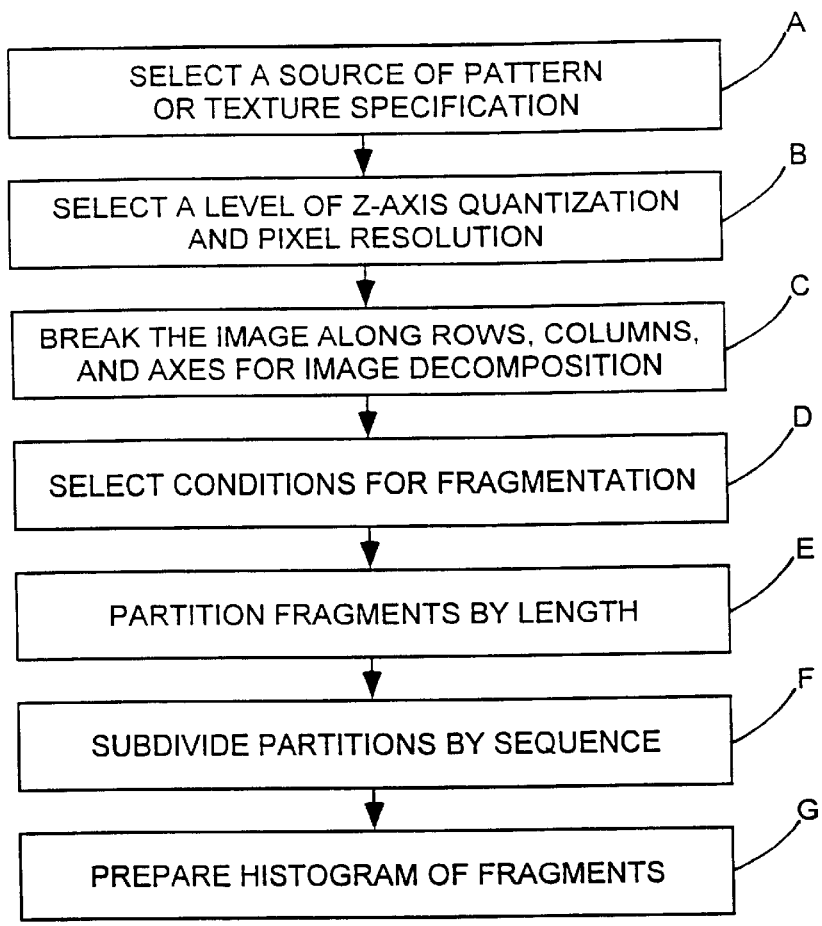
FIG. 2 is a flow chart of a process according to the invention for building a crude probe for texture or pattern matching.

Referring to FIG. 2, there is shown a flow chart of the steps in the texture recognition process according to the invention.

The first step is to select a source of pattern or texture specification, i.e., to select the basis for generating a probe set of data preliminary to establishing the probe set (Step A). Examples are: 1) a complete image, or 2) a "masked" subset of a complete image. Another example is a segment of a dataset (identifiable by an index). Datasets may well include the multispectral datacubes obtained from image spectroscopy or hyperspectral analysis. (In hyperspectral analysis, an image is expanded into a "datacube" wherein each pixel is associated with a set of responses to different wavelengths of light, the response for each pixel being arrayed orthogonally to the plane containing the image. In probing such an image, the index value at the pixel position is wavelength dependent.) While the source may be as simple as a single feature, it may be a complex multidimensional data set. The simpler the source characteristics, the simpler will be the analysis.

In conventional spatial pattern recognition, each point corresponding to a point in space has associated with it a single value or a set of values which represent(s) intensity, color or a component of color. This value will be bounded, i.e., have an upper limit. (Otherwise it would be impractical to take a mathematical complement at that point.) The dataset, to represent any spatial pattern to which can be applied the recognition techniques of the invention, requires such bounds.

The next step in the inventive process of developing a probe is to select a level of graining or quantization resolution per point, plus the level of pixel resolution of a point, across the entire dataset (Step B). The first is the resolution on the index of the value of the "Z" axis quantization of a system of two spatial dimensions. The second is the relative size of a pixel in such a two-dimensional image. In a practical system of the current state of the art, the Z-dimension resolution is typically not greater than 24 bits of color resolution or 8 bits per channel for three channels. Resolutions in the state of the art could be as high as about 48 bits. Resolutions at one or two bits yield information of high contrast only. Low resolution allows fast and simple matching of obvious features. The amount of feature and spatial resolution is directly proportional to the detail to be resolved. The iterative testing of resolution yields an optimal selection for a class of datasets. Higher resolutions are able to resolve finer features. However, there may be a level of resolution which is no longer of interest, such as where the features occurring at a rate greater than a selected spatial frequency cannot be distinguished from noise artifacts.

The third step is to separate or break the image into rows and columns or along polar axes for image decomposition (Step C). The object is to select an orientation or orientations of the two-dimensional image which can be analyzed sequentially in a one-dimensional array. Optimally, the orientation may simplify processing by alignment along a feature. In an interactive system, a user may impose an orientation based on visual selection of features in a texture. Single dimensionality of features enables analysis to proceed based on a close analogy with modern genetic analysis as practiced in the field of biotechnology. At this point, there is only one-dimensional data, so it is possible to use one-dimensional sequence analysis on the underlying pattern/texture matching problem. For higher dimensional patterns, higher dimensional probes can be built and used.

The next step is to select the conditions for fragmentation of the one-dimensional string (Step D). Some of the suitable conditions are threshold values for the first derivative (rate of change) along the string (which could also indicate a gross discontinuity) or the second derivative (acceleration in the rate of change) along the string, the minima or maxima in the string values (where the derivative goes to zero or changes sign). An additional option for fragmentation could be to cleave upon a match with a user-supplied string (e.g., a exact match with a user-supplied string—which is conventional pattern matching—or a fuzzy match or convolution with a user-supplied string, which is also a known pattern matching technique). Cleaving could occur at the exact boundaries of the match or at a preselected offset from a centroid of the match. There are techniques and details of refining the fragment population which could be explored beyond these basic steps.

The next basic step is to partition the fragments into groups (Step E). The groups could be defined by length, average index, "rightedness" and "leftedness" (based on some refinements of the definition of fragmentation), evenness and oddness or the like. And as explained hereinafter shape may also be a basis of partitioning. This classification will help simplify the matching process by minimizing types of probe types to which a fragment must be subjected.

The analysis of the partitioned fragments may then commence with an examination, by partition type (e.g., length), of the number of different partitioned fragments, and subdividing the partitions by fragment type (Step F). This is a step of self comparison. Each fragment is compared with each other fragment in a permutation of comparisons to determine "exact" matches (within the quantization resolution).

The next step following Step F is to prepare a histogram of fragments by partitions (Step G). Each bucket of length n should yield the number "s" of sequence types, based on length. This step yields a primary probe set for detailed analysis at the pixel level. This probe set can be stored in a probe library.

At this point a defined pattern or texture may well have been identified, since a histogram of fragments can be considered a crude signature of a pattern or texture. This is analogous to a genetic analysis in biotechnology wherein nucleic acid fragments are first partitioned by length and then further probed for sequence distributions at that length and separated into a histogram of sizes prior to analysis of the complexity of the sequences. Carrying out such an analysis of genomes of bacteria will produce unique size profiles for each bacterium without any probing of the sequence within the fragments, which in turn identifies the type of the bacterium.

Refining Probes

Figure 3:
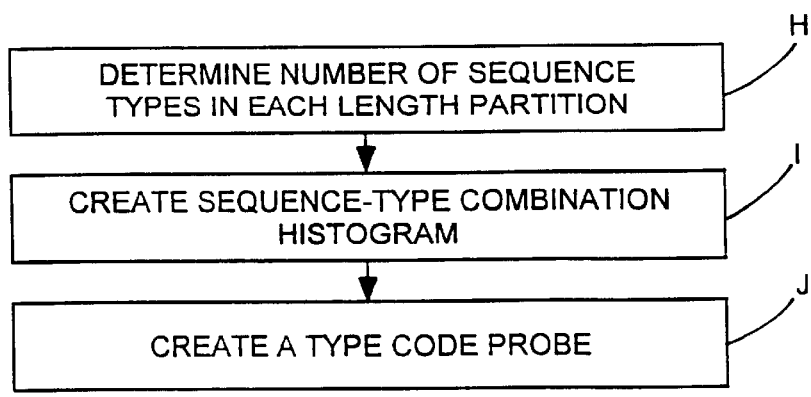
FIG. 3 is a flow chart of one process according to the invention for refining a crude probe, for use in pattern matching with more precision or for use in creating a type code.

FIG. 3 is a flow chart of a process according to the invention for refining a crude probe for use in texture matching with more precision. For each partition, the process first determines the number of different types in each length partition (Step H). The next step is to create a combinatoric histogram within the length categories by listing the number of copies of each sequence type in each partition (Step I). Thereafter this combinatoric histogram information is converted into a type code which lists the detailed histogram and sequence combinatorics of each fragment class, thus yielding a higher order "type code probe" (Step J) for later use. This information can be stored in the probe library. If the type code probe is of very high order, it is a phenotypic-like probe. The present type-code probe is intermediate between the first described genotypic-like probe and a phenotypic-like probe. Thus each fragment of common size is sorted into groups or separated by sequence. A readout of the partitioning of the fragments by length and sequence is a type code.

Figure 4:
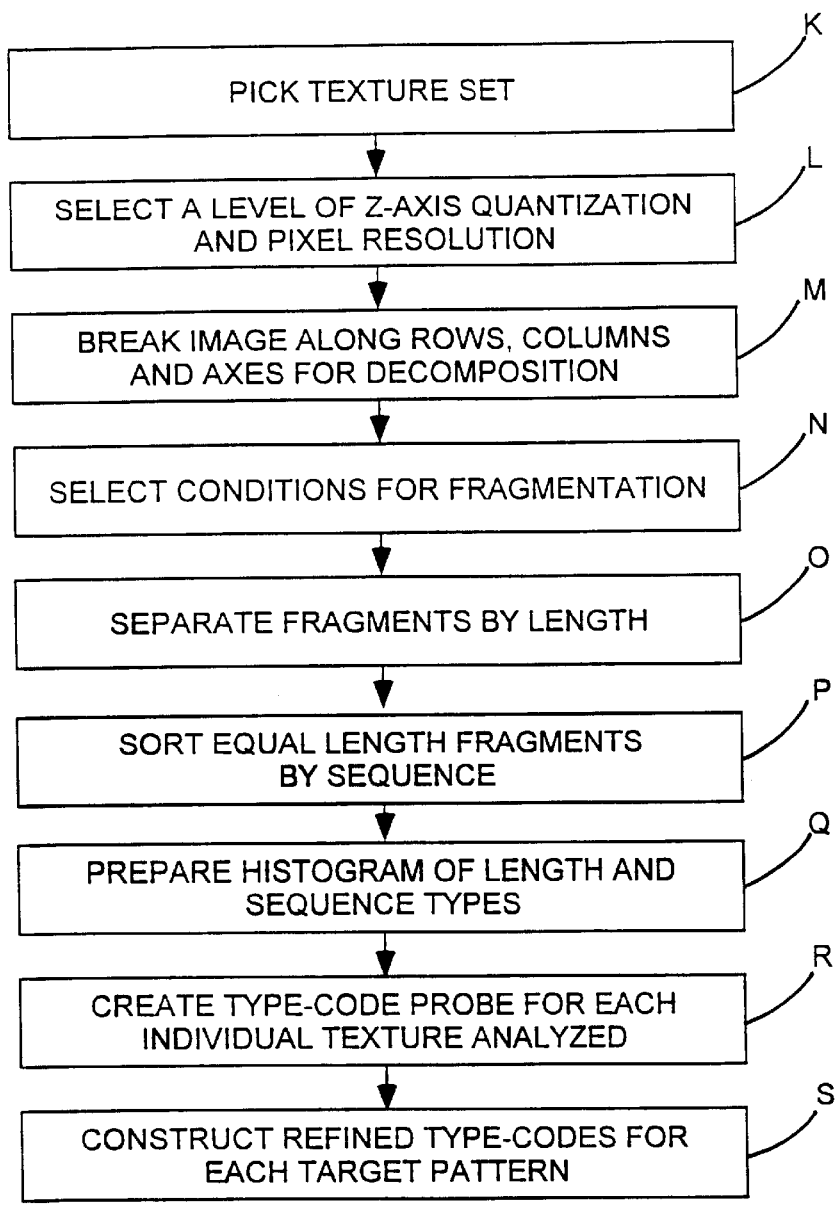
FIG. 4 is a flow chart of a further process according to the invention for refining a probe.

FIG. 4 is a flow chart of a further process according to the invention for refining a type-code probe. This process is an expansion on the method of FIG. 3 and is most useful when the percentages of separated and unseparated fragments must be used to find the pattern of interest. This process refines the production and use of type-code probes like those obtained from the process illustrated by FIG. 3. The first step is to pick a representative set of textures which have a chosen visual range of variation, i.e., set the "range" of the subject (Step K). These textures can range from textures that have a distinct visual appearance and to textures that are only minor variations on a single type. Next the level of z-axis quantization and pixel resolution is selected, i.e., set the "scale" of the subject (Step L). Thereafter the image is broken along rows, columns and axes, i.e., set the "orientation," for decomposition (Step M). Thereafter, the conditions are selected for fragmentation, such as in the technique of FIG. 2, including threshold values along the first derivative (Step N). Next the fragments are sorted and separated by length (Step O). Next the fragments of equal length are sorted by sequence (Step P). Then a histogram of length and sequence types is prepared (Step Q). Next, a type-code probe is created for each individual texture so analyzed (Step R). Next a refined and efficient type-code is constructed for each pattern, which type-code is suitable for uniquely distinguishing its target pattern from among the patterns (Step S). These type-codes are typically feature-rich identifiers so that the process of type-code-to-pattern matching can be quick and efficient, which is one of the objects of the invention. The process of selecting feature-rich type-codes could be automated use of a computer to analyze the samples of patterns and establishing suitable maxima and minima for texture similarity and difference indicative of feature richness.

Figure 5:
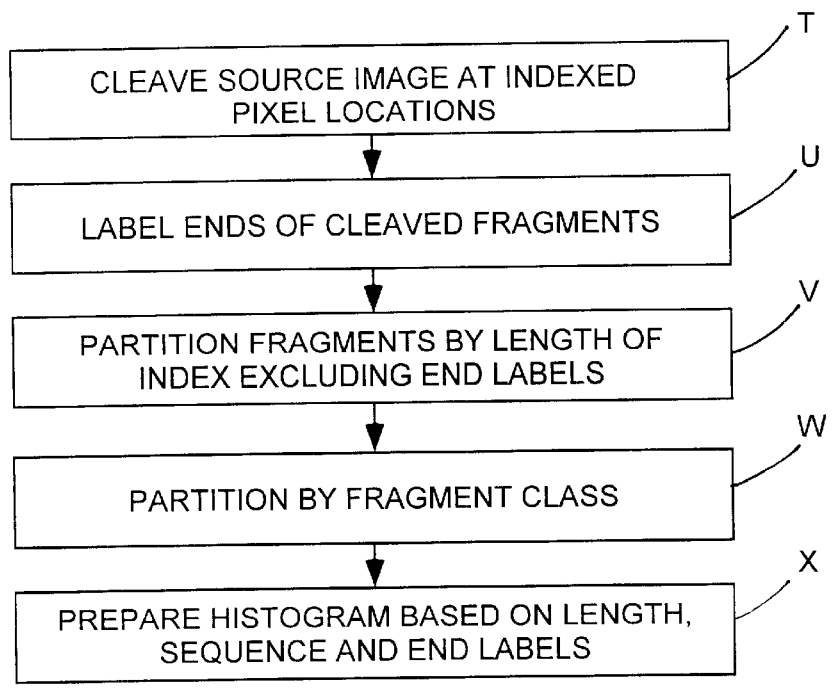
FIG. 5 is a flow chart of a still further process according to the invention for refining a probe.

FIG. 5 is a flow chart of a still further process according to the invention for refining fragment analysis, the creation of the probe set and the distinguishing the type-codes of a probe. Referring to FIG. 2, the process is modified by adding these steps following the condition selecting step (Step D) in order in order to refine the probe set and its analysis with the resultant refinement of the type-code selection process.

Referring to FIG. 6A to FIG. 6E, the steps of fragmentation and end labeling are illustrated. Beginning from a probe source image 100 which contains patterns to be identified for use a probes, the source image 100 has been decomposed into rows 110, 112, 114 of indexed pixels 116, 118, 120 (Step C, FIG. 2). Having selected a condition for fragmentation, the fragmentation process includes cleaving the source image at selected pixel locations 122, 124, 126 (Step T, FIG. 5), then labeling each end of the cleaved locations with tags 128, 130; 132, 134; and 136, 138 (Step U, FIG. 5). Inherent in each of the tags is a value defining the cleavage condition for that particular cleavage. This value is a point in a new type of dataset which can be used for further distinguishing the fragment. Instead of merely partitioning fragments based on the combinatorics of the sequence, the value relates the fragment back to the topological features of the images around which the fragments are generated so that the phenotype can be built back up. For example, this cleavage data point can be used with other image data point to identify an edge or a contour or a color gradient common to multiple rows in a two dimensional image, as might comprise a phenotypic feature.

The next step, similar to Step E, is to partition the fragments by length of the index for the fragment, but excluding the end labels (Step V, FIG. 5). Thereafter the lengths are classified by cutting condition, N×N, where N is the number of cutting conditions among pairs. In the event the cleavage is at a preexisting end which is labeled, there is an addition cutting condition of N×1. The cutting conditions can be ranked to give an order to the sequence for sorting. The step follows of partitioning the fragments by fragment class (Step W). Fragment classes may include at least length and sequence and may include shape information expressed as a sequence, as hereinafter explained, as well as end labeling, such as left end vs. right end to a sequence. The next step, like Step G, is to construct a histogram, but this time based on additional data, such as length, sequence and presence of end labels, and further optionally shape and type of end labels, in order to obtain a richer data set for feature classification and identification (Step X). This allows for better identification of a feature rich subset.

Figure 7:
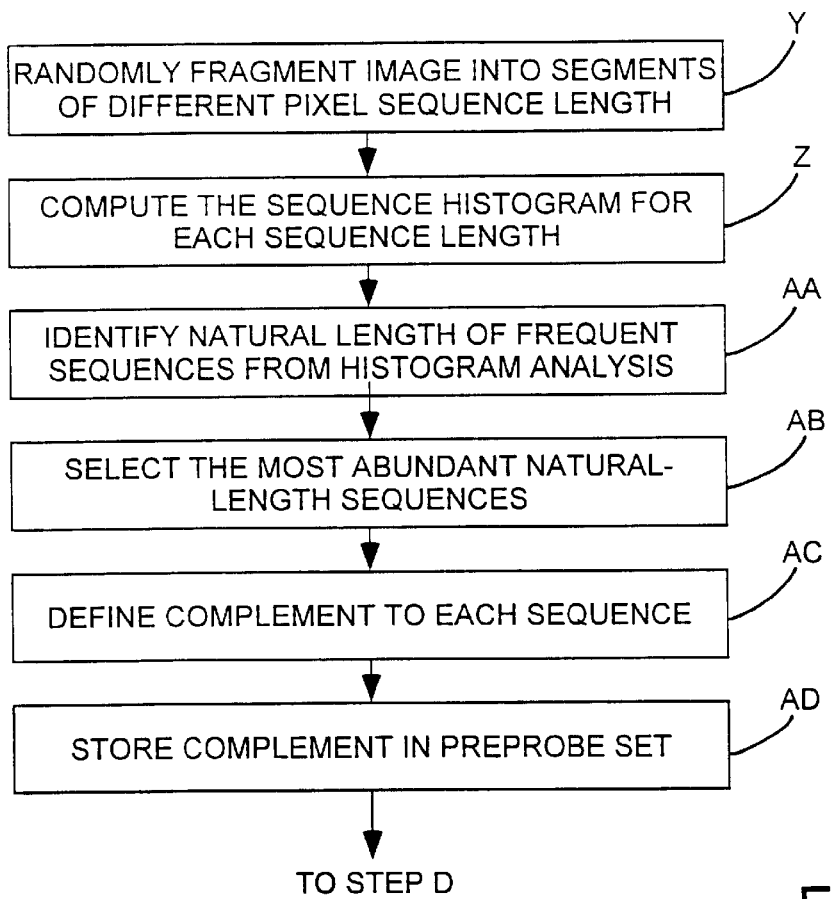
FIG. 7 is a flow chart of a still further process according to the invention for refining a probe using improved fragmentation.

FIG. 7 is a flow chart of a still further process according to the invention for refining a probe using improved fragmentation. Referring briefly to FIG. 2, the step of condition selection for fragmentation is noted (Step D, FIG. 2). As an improvement and precursor, the decomposed image of rows, columns and axes is randomly fragmented into pieces of four to about eight pixels in length (Step Y). At each fragmentation level, the sequence histogram is computed for a chosen length of fragment (Step Z). Thereafter the fragments having those sequences of the most frequent occurrence are identified by examining the peaks in the histogram, i.e., to identify the natural unit sizes for fragments of a known sequence (Step AA). This is a multiple-part process involving examining several histograms at different length indexes. A single histogram is useful for identifying a number of different sequences which occur in high frequency at each selected length. Several histograms at different lengths need to be examined to determine which length for a particular sequence is the natural length. Each sequence of interest can be analyzed essentially simultaneously in the course of this length-frequency analysis. The N-most abundant natural-length sequences are then selected (Step AB). Each one of those sequences then becomes the model for a recognition site sequence in the unknown image and the tool for building the preprobe which looks for that recognition site. To build the preprobe, the sequences so selected from the learning set are used to define a complement to each sequence (Step AC). (This is a simple process: For instance, at each pixel location, wherein for example the pixel value range is 16, those pixels having value 4 are complemented with the value 12 and those pixel values having value 5 are complemented with the value 11, etc. The range quantization serves to introduce flexibility in recognition accuracy.) These complementary pixel strings constitute the preprobe elements to be stored together with other preprobe elements to be further refined into a complete preprobe set (Step AE). The preprobe set is the used in Step D (FIG. 2) to set the conditions for fragmentation. These preprobes can be used to identify the sites for cleavage in the probe fragmentation step in the decomposed source image which generates the probes.

Simulated Hybridization for Using a Probe

Having thus far explained how to produce probes, including by means of producing preprobes, it is now possible to explain how to analyze a target image using the inventive techniques, including simulated image hybridization, an example of an annealing process. The process of matching is, without shortcuts, a computation-intensive process. This invention works very well on a parallel processing computer. It lend itself particularly well to parallel processing analysis because it can be carried out on a one-dimensional sequence independently of other portions of the same data set. The present invention is thus a powerful tool for pattern recognition, albeit not necessarily optimized for specific pattern-matching problems.

Simulated hybridization can be to the image or to the type codes. FIG. 1 can be used is an illustration in connection with simulated hybridization. Hybridization analogies are significant elements which enhance the pattern recognition process to an accuracy well beyond that which is possible with conventional pattern recognition processes, and it confers multiple points of flexibility in the recognition process.

Referring to FIG. 1, a genotype 18 may have an imperfect match with the probe formed around a feature 40. Three interdependent parameters, relating to probability of a match, the strength of the totality of association of a probe with a given target, and the strength of interaction of each index value which makes up a genotype of a probe with its target mating site, provide the flexibility to recognize an imperfect but accurate match. The choice of three constants respectively related with each of these parameters determine the overall fidelity of the pattern matching process. (The choice of these constants may be made iteratively from any seed values which are real positive dimensionless numbers. Conveniently, the value "one" (1) may serve as a seed value for two of the three constants, and the third constant must be chosen to produce the equivalent of a probability between zero and one. The nature of these parameters will now be explained.

The three key parameters for establishing matching criteria are position stringency of position-specific interaction S, sequence stringency of the association of a probe with the target feature D, and stability (as a probability) of the associated target/probe pair in the presence of perturbations P. These represent three different levels of pattern matching weighting: individual pixels, strings or fragments of strings, and groups of strings, where strings correspond to probes.

The position stringency parameter S is given by:

$$S_i = 1/(k_1) * \Delta_i \quad (1)$$

where $S_i$ is the position stringency of position i;

$\Delta_i$ is the difference in the absolute value (or other distance metric measure) at the target pixel and intended complementary value of the probe pixel intended to match with the target pixel ($V_{Ti}$–[1–$V_{Mi}$]; and $k_1$ is the sequence stringency constant (0<K<infinity).

The constant $k_1$ is used to weight the importance of a match at any specific single position to the overall sequence.

The number of individual matches and the contribution of selected individual matches can be weighted independently giving flexibility to the matching criteria for two sequences.

Reorientation and translation of the probe with respect to the target are needed in order to find the maximum across the target of interest. The parameter D is a measure of this match.

The sequence stringency parameter D is given by:

$$D = k_2 * \text{all } S_i \text{ (summed over i)} \quad (2)$$

where

D is the sequence stringency for the entire sequence of the positions of i; and $k_2$ is the weighting constant for the probe(sequence).

The parameter D is a second level of "fuzziness" in matching, so that probes can be weighted relative to one another.

The stability parameter is given by:

$$P = 1/(k_3) * D \quad (3)$$

where $k_3$ is a normalizing and weighting constant.

This constant is useful for favoring strings of clustered elements versus an equal number of separated hits. This is an example of a nonlinear association process. Nonlinear processes are common in biological systems, so the weighting given to clustering supports the continued analogy with this invention.

The stability parameter P is a mechanism for setting, for any probe, a weighted value to be used in connection with a total image analysis. Thus different probes can be weighted differently. If the metric for indicating recognition is based on a summation of all values P for different probes measured against a threshold value, then the weighting P on any particular probe will be indicative of the importance of the contribution of that probe P to the recognition of the total image. Thus there is a third level of "fuzziness" control in the matching of a set of probes with an image.

Furthermore, by making the variation in $K_3$ a function of probe length, one can weight the relative importance of matching the substrings of a probe to the overall pattern matching process.

The above selection of parameters apply directly to the process of simulated hybridization, wherein the elements of a probe and probes are weighted so that various regions of a target image can be more or less emphasized in the recognition process.

Figure 8:
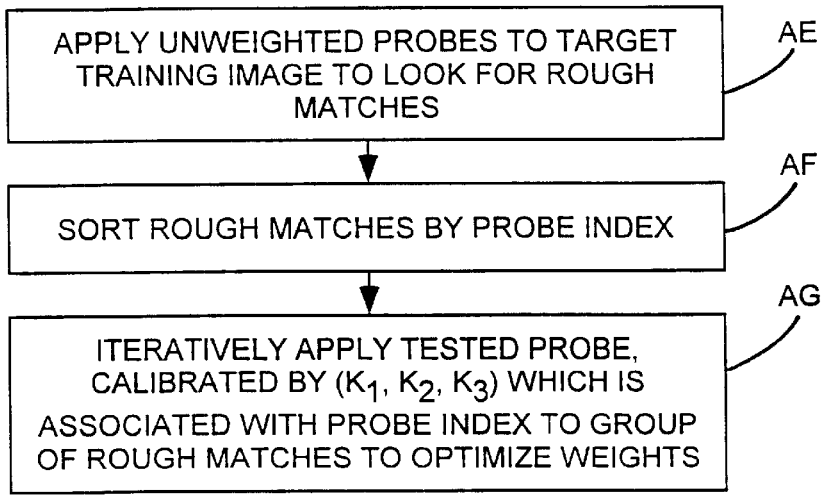
FIG. 8 is a flow chart of a still further process according to the invention for a process for determining and refining probing conditions using simulated hybridization.

FIG. 8 is a flow chart illustrating the training portion of the recognition process using this weighting method, namely a method of simulated hybridization. First, a set of unweighted probes is applied to a target training image to determine as a presumably rough cut any matches between the probe and the target image (Step AE). Second, the strings which are rough probe matches are sorted by probe index, in order to group the strings of rough matches with selected probes (Step AF). Third, the probe weights are trained by iteratively applying, for each probe index, the probe with various weights to the group of rough matches (Step AG). Weights are optimized in this manner to yield the minimal set of probes which selectively and completely identify the target(s) from which the probes are made. This process lends itself to the use of neural net tools. Parallel processing computers such as the massively-parallel Connection Machine pioneered by Thinking Machines Inc. provides a suitable platform, whether or not the neural net paradigm is used for analysis. Conventional sequential processors can be used as well, if speed is not critical.

This set of weighted probes can then be used, according to the invention, in analysis of unknown images, to determine if all or part of the probes correspond (by whatever closeness criteria is chosen) with one or more elements in the target image. The probes should produce a very good match if the target image is related to the target training image, and especially if the pixel resolution is approximately the same. Since this process involves pixel-level matching, those cases wherein the target is present at a different scale or resolution must be processed using the type code method herein described to assure match. The process of applying weighted probes is analogous to the biological process of hybridization.

Figure 9:
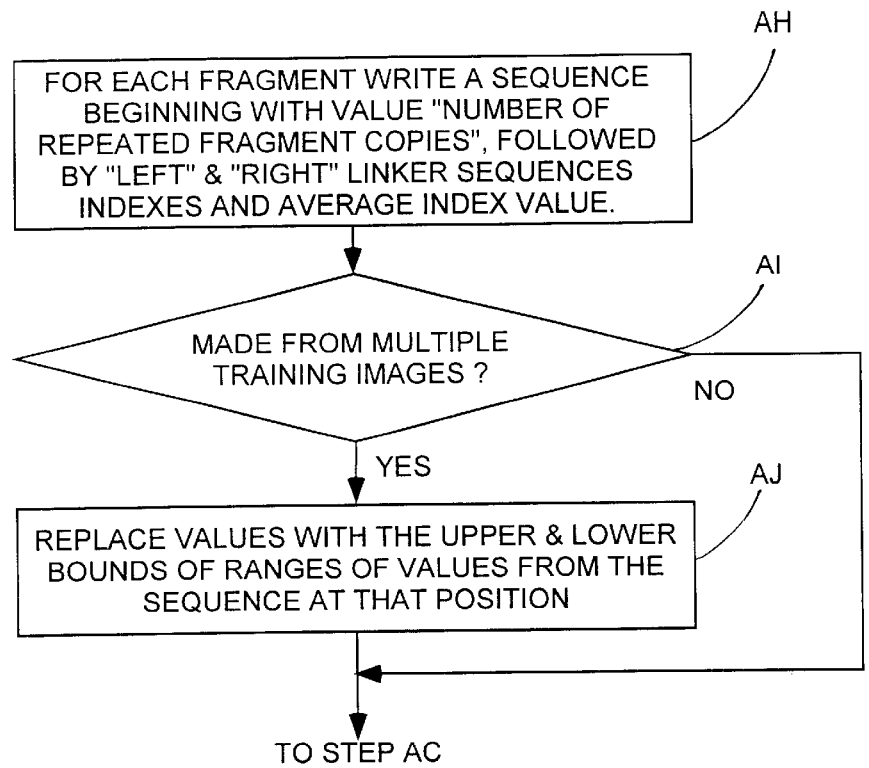
FIG. 9 is a flow chart of an inventive process of producing a sequence type-code from a target image and from the images to be processed.

FIG. 9 is an illustration of the process of producing a type code from a target image and from the images to be processed. Type codes are a listing, in a higher order sequence, which capture the key features of the histogram analysis of the fragment population. Type codes can be generated from both probes and from the target images. Beginning with the most abundant fragment in the histogram obtained from the process of FIG. 2 (Step G), for each fragment of the histogram, up to the cutoff, a sequence is written which follows a uniform method. The first entry is the number of copies of the most abundant fragment, followed by the fragment length, tag information regarding the cutting condition (left and right linkers) index, and average index value. Finally the sequence can be listed in its entirety. (Step AH). The set of fragments may be made from multiple training images. Hence the set is tested for multiple image sources (Step AI). If none is found, then the set is passed on to Step AC (FIG. 7) for further processing. If multiple image sources are found, then the values found are replaced, in the set, with the upper and lower bounds of the ranges of values from the sequence in that position (Step AJ), and the process proceeds at Step AC.

Figure 10:
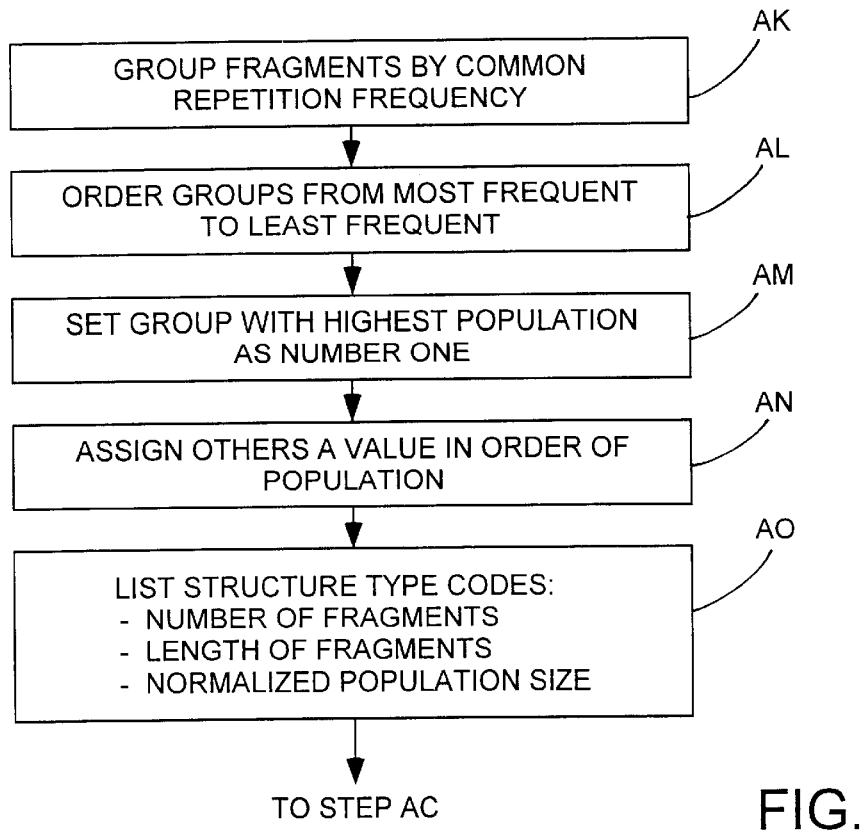
FIG. 10 is a flow chart of an inventive process of producing a structural type-code from a target image and from the images to be processed.

FIG. 10 illustrates a method for producing a structural type code for simulated hybridization. A structural type code is useful for establishing an absolute scale of the feature being sought. This allows the system to find a similar target present in different absolute sizes in potential target images. Therefore, structural type code generation typically precedes sequence type-code generation.

Referring to FIG. 10, the fragments are first grouped according to common repetition frequency (Step AK). The groups are then ordered or sorted from the most populous to the least populous (Step AL). The group having the highest population is denoted as number 1, so that the most populous group becomes the normalized group (Step AM). All other groups are then assigned a fractional value of 1, depending upon their relative population compared with the most populous group (Step AN).

The structural type code can then be extracted by listing the number of fragments, the length of the fragments, and the normalized population size (Step AO). The length of the fragments provide a resolution-independent measure, which is useful for allowing a probe set to recognize a common object at different resolutions and scales. The process then proceeds at Step AC of the hybridization steps.

Figure 11:
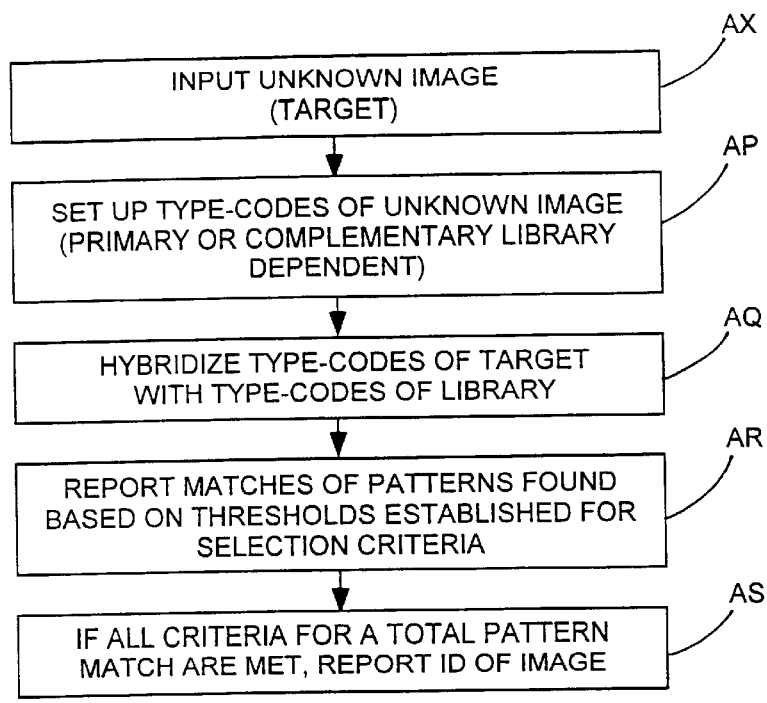
FIG. 11 is a flow chart of analysis of a target image using simulated hybridization of type-codes.

FIG. 11 is a flow chart of analysis of a target image using simulated hybridization of type-codes. Commencing from the results of the histogram collected in the process of FIG. 2 (Step G), assuming that type-codes have been developed for probes and targets in an image "genetic" library, the type-codes can now be applied in an "on-line" process to investigate a target image of unknown character for pattern matches. Given the input of unknown target image (Step AX), type codes are set up for the unknown target image which are complementary to the type-codes stored in the image library (Step AP). The type codes in the image library can be either "normal" or "complementary" based on the previously-described processes. The probe type-codes of the patterns in the library are then hybridized to the complementary type-codes of the target image, i.e., the lock and key process is applied using the parameters which define type-code (Step AQ). Once a match between a probe and a target type-code is found, a report is given that a match of a pattern has been found (Step AR). The state of a type-code match is based on thresholds previously established for the pattern selection criteria. Thus, a list of matches is established for the target image. Further analysis can then be applied, using more conventional pattern and sequence matching techniques, to determine if the list of matches and their placement in the list correspond to a predefined image, and if so, then a report of the identification of a particular image is made (Step AS). It is also possible to use methodology according to the invention, as for example explained in connection with FIG. 8, to further discriminate preliminary matches by adjustment of the simulated hybridization constants. In this way the population of preliminary matches would already include the refined characteristics, so that preliminary matches are likely to be accurate.

Figure 12:
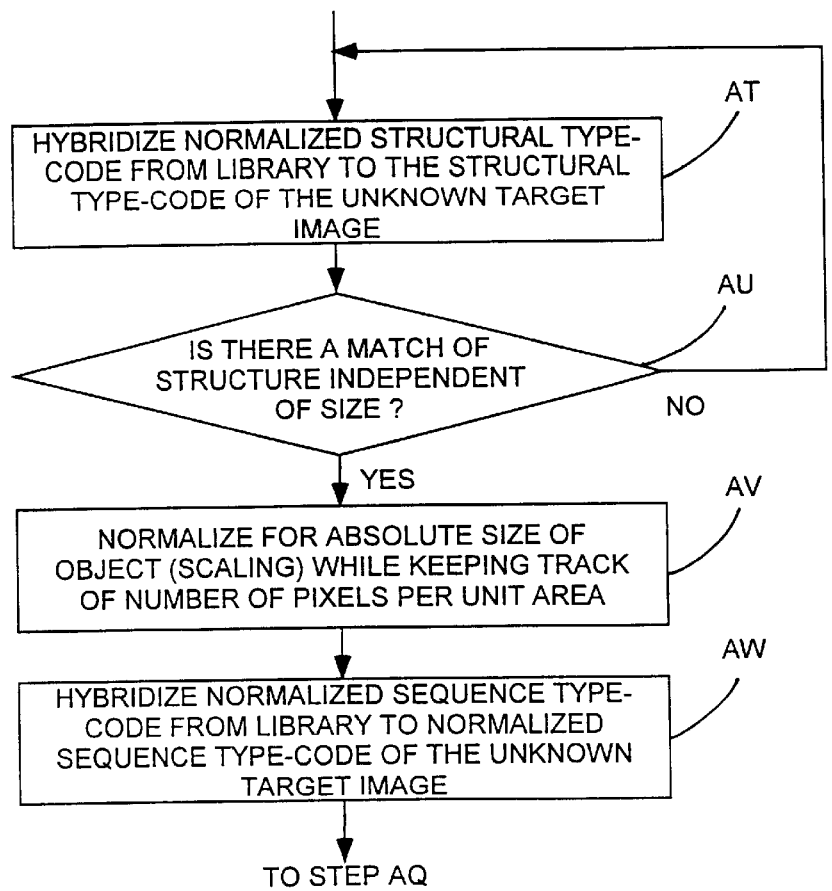
FIG. 12 is a flow chart for an inventive process using structural and sequence type-code probing in order to normalize probes for proper scale and resolution.

FIG. 12 is a flow chart for an inventive process of probing of type-codes in order to normalize probes for proper scale and resolution. Both structural and sequence type-codes, developed according to the processes of FIG. 10 and FIG. 9, respectively, are employed. The indices in the type-codes can actually be used to produce a visual type-code image wherein the patterns (phenotypes) of interest can be visually identified. Commencing from the results of the histogram collected in the process of FIG. 2 (Step G), developed from the improved (structure and sequence type-code-based) processes, and wherein the library has already been normalized, it is necessary to normalize the type-codes of the unknown target image. This is a step which typically precedes Step AQ as part of Step AP. First, for each pattern investigated and using the library of type-codes, the structural type-code from the library is hybridized to the structural type-code (complementary in form) of the unknown target image (Step AT). The test of structural match is independent of size (Step AU). If a match is not found, then the process is repeated with the next probe; otherwise, if a match is found, then size of the object is normalized, i.e. scaled, to fit with the scale of the library type-code (Step AV). This normalization could be as simple as finding a common denominator between parts of type-codes. It is useful to keep track of the pixel resolution (pixels per unit area) in order to recover the image data. Finally, the sequential type-code from the library is hybridized to the normalized sequence type-code (in complementary form) of the unknown target image to determine if there is a more precise match (Step AW). The process of recognition then continues at Step AQ.

Once the sequence type-code is normalized, it is possible to reverse the process of FIG. 3 which generates the sequence type-codes from the histogram and instead reconstruct the fragment distribution from the sequence type-code and write them (recompose) at the new normalized resolution to identify the key features found in the sequence type-codes. In addition, the newly-scaled sequence type-codes can be used to visually "probe" an unknown target image for key features using a display showing the matches produced by simulated hybridization. The display of simulated hybridization would show what features match visually on an image.

Figure 13:
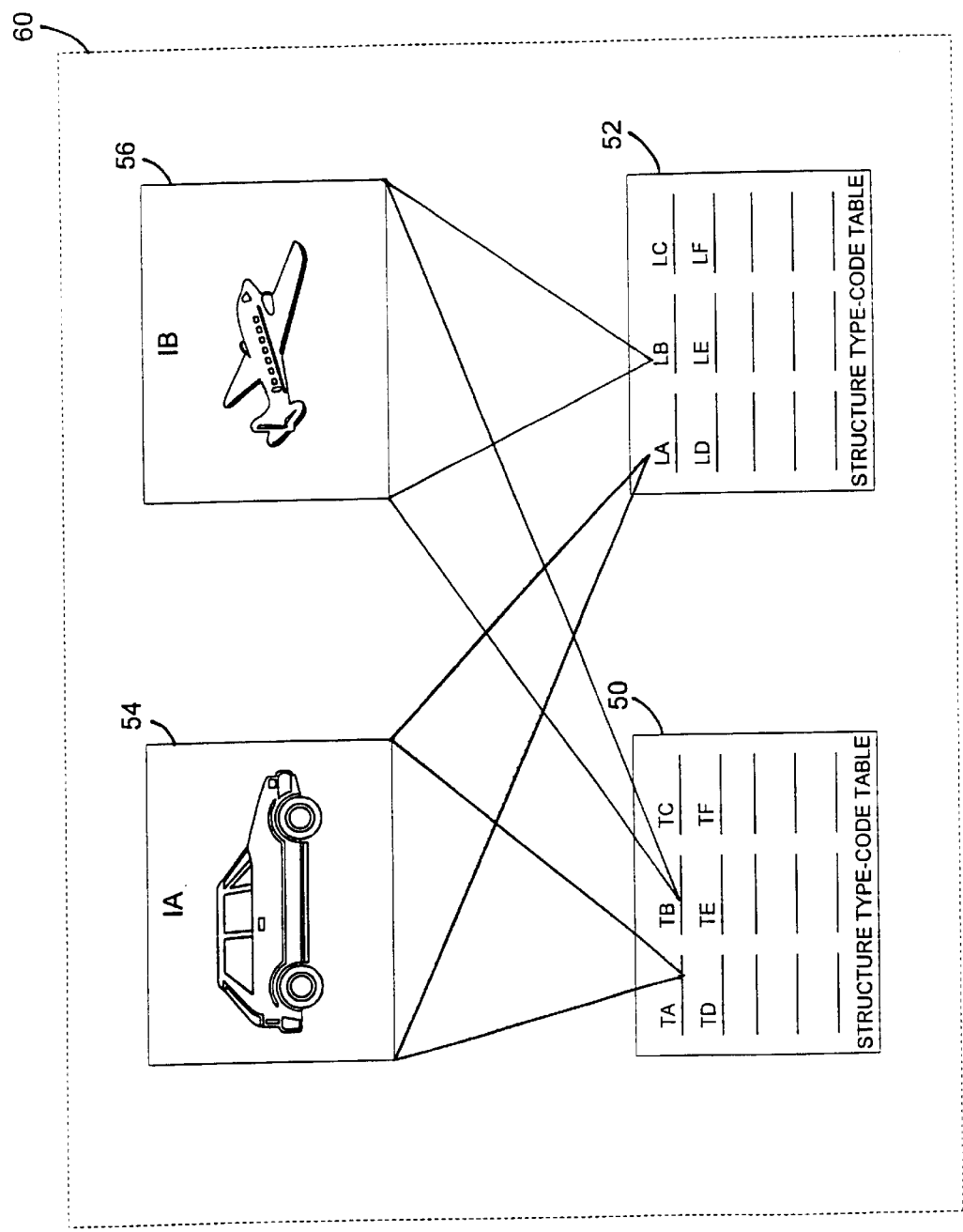
FIG. 13 is an illustration showing the relationships of image level structural type-codes in an first array and image level sequence type-codes in a second array with a plurality of images in an image database.

FIG. 13 is an illustration showing the relationships of image level structural type-codes in an first array 50 and image level sequence type-codes in a second array 52 with a plurality of images 54, 56 in an image database 60. Image 54, labeled IA, and image 56, label IB are but two records of raw two-dimensional data in the image database. The records are a flat field of typically one million pixels (with typically up to 24 million bits of data each for an 8-bit resolution color image). The image can be described in terms of fragments, or strings, of pixels. Fragments represent single, one-dimensional features. It is typical for a moderately-complex image to have as many as 20,000 fragments, each fragment containing several hundred bits (the sum of which is the number of bits in the image). Each fragment can be represented by a type code of structure and a type-code of sequence. A type-code can apply to many different fragments, the collection of which can be catalogued by a histogram over the range of type codes. The histogram can be truncated at any level to report only the most abundant of fragments.

Each image can be represented by a single image-level type-code pair, such as pairs TA, LA; TB, LB; TC, LC; TD, LD; TE, LE; TF, LF, and so on throughout the paired tables 50 and 52, as well as by a collection of object or feature-level type codes. The type-codes may serve as an index to the image database. It should be understood that an image database is constructed both for the training images and for the unknown images. In the instance of training images, probes are developed. In the instance of unknown images, probes previously developed are applied to the database which contains the unknown images in which the patterns being sought might occur in order to attempt to identify those patterns associated with the probes. In each instance the values along the probes are complementary to the genotypes of the image.

Figure 14:
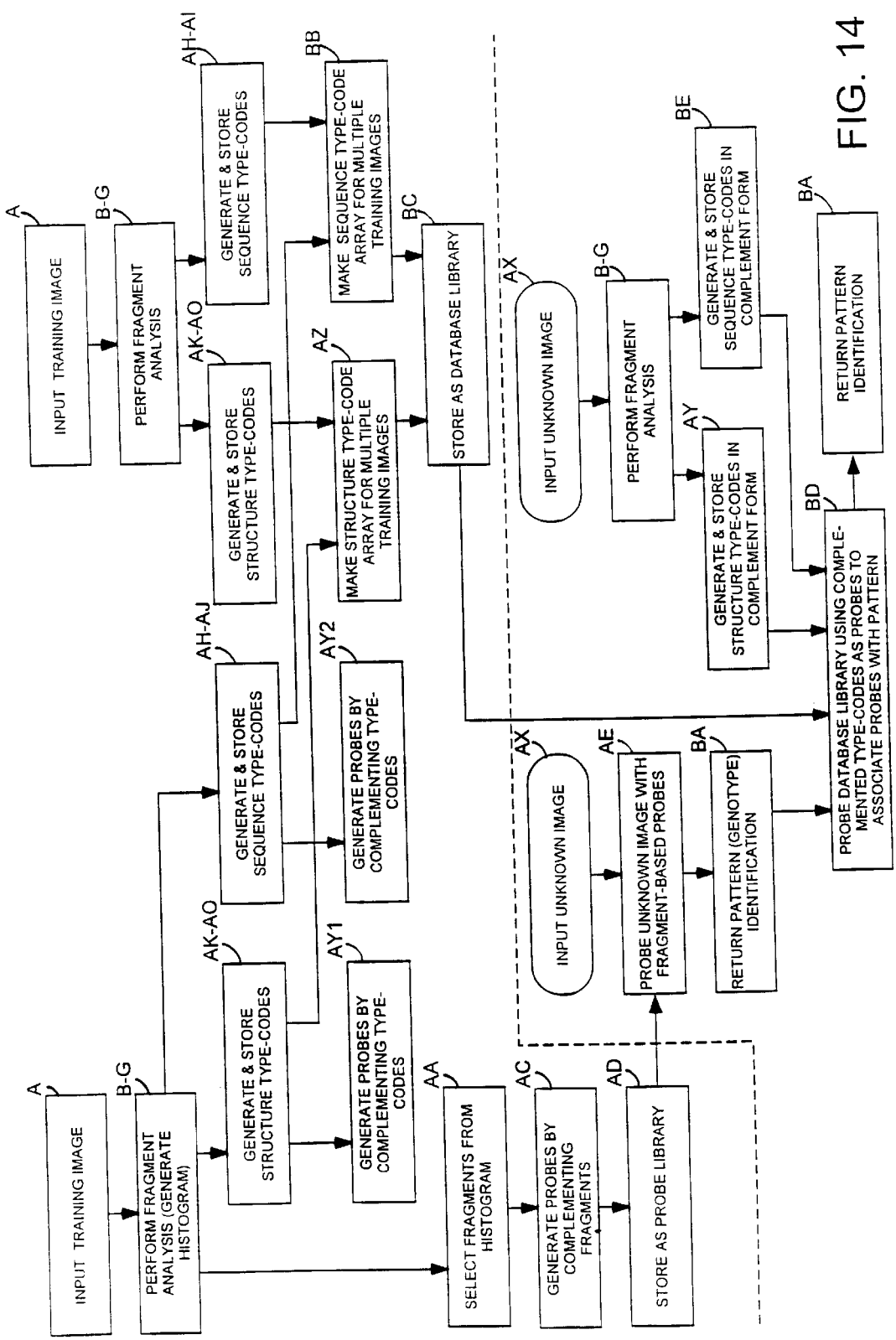
FIG. 14 is a flow chart of the overall inventive processes.

FIG. 14 is a flow chart of the overall inventive process. Referring concurrently to FIG. 13, which is the image-table depiction, and to FIG. 15, which is a block diagram of an apparatus for performing the processes according to the invention, the first steps are to individually input the training images 54, 56 (Step A) via an input device 70, such as a scanner or video capture device, and then process the training images 54, 56 to a fragmenter/fragment analyzer 72 to generate histograms of the fragments (Steps B–G). Along one path, a probe generator is used to generate a set of genotype-level probes by selecting fragments from the histogram (Step AA) and generating probes by complementing the fragments (Step AC). The probes are then stored in a probe library (Step AD) in a probe set storage device 76A, such as a CD-ROM, disk drive, tape or the like.

In parallel to the probe generator is a type-code generator and storage element 78. Using data from the histograms for each image, the type-code generator prepare a structure type-code table 50 (Steps AK–AO) and a sequence type-code table 52 (Steps AH–AJ). A type-code probe generator 80 generates probes from type-codes (Steps AY1 and AY2) by merely complementing the structure type-codes and the sequence type-codes. Since the type-codes are already stored and the process of complementing is extremely fast, there is no need to provide additional storage in order to use the type-code based probes. However, such probes optionally could be stored in probe set storage 76B.

Arrays of type-codes can be assembled in an array builder 82 in which the steps are making a structure type-code array 50 for multiple training images (Step AZ) and making a sequence type-code array 52 for multiple training images (Step BB). The two arrays 50, 52 are stored in an array storage device 84 as a representation of a database library (Step BC). The indexed type-code data obtained at this step can be used to produce images for inspection.

The foregoing summarizes the offline processes according to the invention. The stored probes or equivalents are then available to search unknown images in online processes. An unknown image or set of images 86 is provide through an appropriate input device 88, which could be live, or be provided via analog media or digital media. At the genotype level, the fragment-based probes can be used to probe the image in a genotype comparator 90 (Step AE), returning a genotype ID (Step BA).

At the phenotype level, a genotype-like comparison is then performed by a phenotype comparator 92 on the information obtained by other analyses, including hybridization as the mechanism of genotypic comparison, or simple string matching (Step BD). Using the genotype ID as a sequence type-code for a feature of the target image in a sequence comparison, and using a 94 to establish fragments, a type-code generator/phenotype comparator 92 receives the genotype ID, a fragmenter 94 provides, from the unknown or target image 86, selected fragments (Steps B–G) from which a type-code generator 96 generates type-codes (Step AY and BE). Then, comparing the complemented type-codes of the source image and the probes of the target image, the candidates for image elements are identified. The probing of the type-codes identifies features that are not evident in single-genotype comparisons.

Finally, the database library 50, 52 may be probed in parallel in the phenotype comparator 92 using multiple probes, if desired, to enhance the speed of with which pattern recognition can be carried out on large numbers of images.

While a software program listing would enhance the understanding of the details of the invention, a programmer or technician skilled in the art could readily produce an operational system from the foregoing description without undue experimentation. Detailed explanation of selected steps needed to implement aspects of the invention is therefore unnecessary.

To increase the level of information extracted from the fragment under analysis, the method according to the invention can be refined by examining shape indicia so that the probe examines not only position-based information of the first order in color space or any other space of "n" variables, such as data space, but relative position information (differences in image values), i.e., position-based information of the second and higher orders. Specifically, in the process described in connection with FIG. 2, FIG. 3 and FIG. 4, further steps are added to partition fragments by shape in color space (a Step E'). Shape is explored through the first, second and third derivatives of the differences between RGB values. For example, by taking the second derivative, minima and maxima in the first derivative can be determined. Minima and maxima of the first and second derivatives are sufficient to extract virtually all useful shape information from a sequence. As a practical matter, derivatives below a predetermined threshold are assumed to be zero. Segmentation algorithms have been designed to key on the points in the sequence of minima and maxima, as in Step F. The type code probe created according to this aspect of the invention thus includes length, sequence and shape (Step J, FIG. 3.), the determining step (Step H) is to determine the number of shape and sequence types in each length partition, and the histograms are of shape and sequence as functions of length (Step I). In the process associated with FIG. 4, a step is provided as Step O' after Step O wherein there is a further partitioning of fragments of equal length by shape and sequence. Thereupon Step P becomes the step of sorting by the keys of shape and sequence. The histograms are modified to be of shape and sequence as functions of length (Step Q).

The inventive process could be carried out in other media, such as using conventional DNA technology. For example, a two-dimensional image to be studied is transferred into a two-dimensional medium that is biologically active. Thereupon probes bearing a suitable identifying marker can be introduced onto the medium. Where the probes stick to the medium, recognition is declared. Location would be noted by an appropriate detector. Identity would be revealed by marker identification. Gene chip technology is one mechanism for marker identification and detection, while a visible scan is another.

The invention has now been explained with reference to specific embodiments. Other embodiments will be apparent to those of ordinary skill in the art, as noted above. It is therefore not intended that this invention be limited, except as indicated by the appended claims.

What is claimed is:

1. In a computing machine, a method for mapping a dataset representative of physical features to a specific pattern representative of physical objects wherein said dataset can be mapped intermediately to a spatially-defined image, said method comprising:

selecting a basis for generating at least one probe set of data from a training dataset;

creating at least one probe set composed of probes of partitionable, spatially-definable data from said training dataset on said computing machine for mating with patterns in known spatially-definable images to be recognized, each said probe of said probe set having a complementary value at selected image fragment positions among a preselected fraction of image fragments in key features in the spatially-defined image;

inputting an unknown dataset to said computing machine;

separating said unknown dataset into an ordering for decomposition;

segmenting said unknown dataset into partitions corresponding to segmentation on said training dataset;

applying said at least one probe set to said unknown dataset to identify with said patterns; and outputting said patterns associated with said selected image fragment positions of said unknown dataset specifying representations of physical objects associated with said patterns.

2. In a computing machine, a method for mapping a dataset representative of physical features to a specific pattern representative of physical objects wherein said dataset can be mapped intermediately to a spatially-defined image, said method comprising:

creating at least one probe composed of spatially-definable data on said computing machine for mating with patterns in known spatially-definable images to be recognized, each said probe having a complementary value at selected image fragment positions among a preselected fraction of image fragments in key features in the spatially-defined image;

inputting said dataset to said computing machine;

applying said at least one probe to said input dataset to identify with said patterns; and outputting said patterns associated with said selected image fragment positions of said dataset specifying representations of physical objects associated with said patterns, wherein said probe creating step comprises:

selecting a basis for generating a probe set of data preliminary to establishing the probe set;

selecting a level of graining or quantization resolution per point, and a level of pixel resolution of a point, across the entire dataset;

separating the dataset into an ordering for decomposition such that the dataset can be analyzed sequentially in a one-dimensional array;

selecting conditions for fragmentation of the one-dimensional string;

segmenting said one-dimensional string according to partition type; and preparing a histogram of fragments by said partitions.

3. The method according to claim 2 further including the steps of:

determining the number of different types in each length partition;

creating a combinatoric histogram within length categories with the number of copies of each sequence type in each partition; and converting said combinatoric histogram information into a type code that lists detailed histogram and sequence combinatorics of each fragment class into order to yield a type-code probe.

4. The method according to claim 3 further including the steps of:

picking a representative set of textures that have a range of variations;

selecting the level of z-axis quantization and pixel resolution;

decomposing the dataset along rows, columns and axes to set orientation for further decomposition;

selecting conditions for fragmentation into fragments;

sorting said fragments by at least length;

sorting fragments of equal length by sequence;

preparing a histogram of length and sequence types;

creating a type-code probe for each individual texture; and constructing a type-code for each pattern.

5. The method according to claim 3 further including the steps of:

normalizing the type-codes;

hybridizing to the type-codes for each pattern investigated using a library of type-codes;

testing on a library type-code for a structural match with a probe;

if a structural match is not found, repeating the testing step with a next probe; otherwise, if a match is found, normalizing size to fit with the scale of the library type-code; and hybridizing a corresponding sequential library type-code to a normalized target image sequence type-code in complementary form to determine if there is a more precise match.

6. The method according to claim 5 further including the steps of preparing a structure type-code for said library of type-codes comprising:

grouping image fragments according to common repetition frequency to obtain groups;

ordering said groups from most populous to least populous;

designating the group having the highest population as the normalized group of value of 1;

assigning all other groups a fractional value of 1 based upon relative population compared with said normalized group; and establishing structural type-code by number of fragments, length of the fragments, and normalized population size.

7. The method according to claim 6 for probing a target with a type-code from said type-code library comprising:

inputting an unknown target image;

setting up type-codes of the unknown target image, said target type-codes being of a form that is complementary to probe type-codes stored in the image library;

hybridizing the probe type-codes of the patterns in the library to the complementary target type-codes of the target image;

reporting an image identification match upon finding a meeting of a threshold of preestablished closeness criteria and number criteria between probe type-codes and target type-codes.

8. The method according to claim 7 wherein said probe type-codes of said image library are a collection of structural type-codes and of sequence type-codes.

9. The method according to claim 2 further including the steps of:

cleaving the source dataset at selected pixel locations to yield end locations on each fragment;

labeling each end location with tags with a value defining local cleavage condition;

partitioning the fragments by length of the index for the fragment, while excluding the end labels;

classifying the lengths by cutting condition;

partitioning the fragments by fragment class;

constructing a histogram based on additional data, including length, sequence, presence of end labels, shape and type of end labels, in order to obtain a dataset for feature classification and identification.

10. The method according to claim 2 further including the steps of:

randomly fragmenting a decomposed dataset into fragments formed of groups of elements;

computing for selected lengths of fragments a sequence histogram at each fragmentation level;

examining peaks in histograms for the fragments having those sequences of the most frequent occurrence to identify the natural unit sizes for fragments of a known sequence;

selecting most abundant natural-length sequences for use as a model for a recognition site sequence and as a tool for building a preprobe; and building the preprobe as a complement to each sequence so selected.

11. In a computing machine, a method for matching unknown information patterns representative of physical features organized into a set of discrete multidimensional data which can be represented in an array with a topology, wherein the array can be mapped intermediately to a spatially-defined image space of discrete elements which are definable along axes with boundaries, said method comprising:

creating at least one probe set composed of probes of partionable, spatially-defined data which is complementary at a genotype level with patterns to be recognized in the image space, each said probe having a complementary value at selected image fragment positions of at least the first order among a preselected fraction of image fragments in key features in the image space; and employing said probe set to identify and locate said patterns within the image space wherein said employing step comprises inputting said n-dimensional data to said computing machine;

applying said at least one probe set to said input n-dimensional data to identify with said patterns; and outputting said patterns associated with said selected image fragment positions in order to specify physical objects associated with said patterns.

12. The method according to claim 11 further including:

building a collection of different probes for perceiving different patterns within the image.

13. The method according to claim 11 further comprising:

building a collection of said probes for use together; and employing said group of probes to identify features at a phenotype level.

14. In a computer system, a method operative on information patterns representative of physical features in a set of discrete multidimensional data which can be represented in an array with a topology, wherein the array that can be mapped to spatially-defined image space of discrete elements, for determining similarity between two complementary sequences, said method comprising the steps of:

creating a probe which is complementary at a genotype level with patterns to be recognized in the image space, said probe having a complementary value at selected image fragment positions of at least the first order among a preselected fraction of image fragments in key features in the image space;

employing said probe to identify and locate said patterns within the image space, said probe-employing step comprising the steps of:

applying a set of unweighted probes formed of datasets to a target training image to determine as a presumably rough cut any matches between individual probes and the target image to obtain strings;

sorting the strings which are rough probe matches by probe index, in order to group the strings of rough matches with selected probes;

training probe weights by iteratively applying, for each probe index, the probe with various weights to the group of rough matches; and optimizing weights to yield a minimal set of probes which selectively and completely identify targets from which the probes are made.

15. An apparatus for matching information patterns in a set of discrete multidimensional data, which can be represented in an array, with a physical topology, where the array that can be intermediately mapped to a spatially-defined image in an image space of discrete elements which are definable along axes with boundaries, said apparatus comprising:

means for creating at least one probe set composed of probes of partitionable, spatially-definable data from a training dataset, each said probe being complementary at a genotype level with known spatially-definable patterns to be recognized in the image space, each said probe in said probe set having a complementary value at selected image fragment positions among a preselected fraction of image fragments in key features in the spatially-defined image in the image space;

means coupled to said probe-creating means for storing said probe set; and means for employing said probe set to identify and locate said patterns within the image space, wherein said employing means comprises dataset input means coupled to said computing machine for inputting an unknown dataset;

segmentation means for segmenting said unknown dataset into partitions corresponding to segmentation in said training dataset;

probe application means for probing said unknown dataset to identify with said patterns; and pattern output means for outputting patterns associated with said selected image fragment positions of said dataset and specifying representations of physical objects associated with said patterns.

16. An apparatus for matching information patterns representative of physical objects in a spatially-defined image, said apparatus comprising:

a probe creator means for making at least one probe set of probes for patterns in an unknown image to be recognized from patterns extracted from a model image, each said probe having a complementary value at selected pixel positions among a preselected fraction of image pixels in key features in the model image;

a storage mechanism coupled to said probe-creator means for storing said probe set; and a probe applicator and detector employing said probe set to identify and locate said patterns within the image under test; and output means for outputting identity and location of said patterns.

* * * * *